United States Patent
Inoue et al.

(10) Patent No.: US 10,149,435 B2
(45) Date of Patent: Dec. 11, 2018

(54) COMBINE

(71) Applicant: Kubota Corporation, Osaka-shi (JP)

(72) Inventors: Hirotsugu Inoue, Sakai (JP); Kazuhiro Takahara, Sakai (JP); Hiroshi Ikeda, Sakai (JP); Kazunori Matsufuji, Sakai (JP)

(73) Assignee: Kubota Corporation, Osaka (JP)

( * ) Notice: Subject to any disclaimer, the term of this patent is extended or adjusted under 35 U.S.C. 154(b) by 514 days.

(21) Appl. No.: 14/785,943

(22) PCT Filed: Feb. 4, 2014

(86) PCT No.: PCT/JP2014/052537
§ 371 (c)(1),
(2) Date: Oct. 21, 2015

(87) PCT Pub. No.: WO2014/174869
PCT Pub. Date: Oct. 30, 2014

(65) Prior Publication Data
US 2016/0066507 A1  Mar. 10, 2016

(30) Foreign Application Priority Data

Apr. 26, 2013  (JP) ................................ 2013-093920

(51) Int. Cl.
*A01D 41/127* (2006.01)
*A01F 12/50* (2006.01)
(Continued)

(52) U.S. Cl.
CPC ........ *A01D 41/1277* (2013.01); *A01B 79/005* (2013.01); *A01D 41/127* (2013.01);
(Continued)

(58) Field of Classification Search
CPC ............ A01D 41/1277; A01D 41/1272; A01D 41/127; A01D 41/1208; A01D 41/1274;
(Continued)

(56) References Cited

U.S. PATENT DOCUMENTS

| 5,487,702 A | 1/1996 | Campbell et al. |
| 5,991,025 A * | 11/1999 | Wright ...................... G01J 3/02 356/328 |

(Continued)

FOREIGN PATENT DOCUMENTS

| CN | 201194484 Y | 2/2009 |
| EP | 0042245 A1 | 12/1981 |
| JP | 0347014 A | 2/1991 |
| JP | H0347014 A | 2/1991 |
| JP | 10313638 A | 12/1998 |
| JP | 2002223629 A | 8/2002 |
| JP | 2002262649 A | 9/2002 |

(Continued)

*Primary Examiner* — Robert E Pezzuto
(74) *Attorney, Agent, or Firm* — The Webb Law Firm (57) ABSTRACT

A combine includes: a yield measurement container (32) having a yield receiving opening (32a) for receiving at least some of grains supplied to a grain tank (15) which accumulates grains obtained by threshing, a yield discharge opening (32b) for discharging received grains, and a yield shutter (34) for opening and closing the yield discharge opening (32b); a yield measurement section for detecting, while the yield shutter (34) is closed, that a predetermined volume of grains has been accumulated in the yield measurement container (32) and then outputting a detection signal; a time calculation section for calculating, based on the detection signal, an accumulating time required to accumulate the predetermined volume of grains; and a yield calculation section for calculating a yield per unit travel based on a travel speed and the accumulation time.

11 Claims, 9 Drawing Sheets

(51) Int. Cl.
*A01B 79/00* (2006.01)
*A01D 41/12* (2006.01)
*G01N 33/10* (2006.01)

(52) U.S. Cl.
CPC ..... *A01D 41/1208* (2013.01); *A01D 41/1272* (2013.01); *G01N 33/10* (2013.01)

(58) Field of Classification Search
CPC .............. A01D 41/1275; A01D 43/085; A01D 79/005; B07C 5/342; B07C 5/368; G01J 3/02; G01J 3/28; G01J 3/2803; G01J 3/42; G01J 3/50; G01N 21/359; G01N 21/3563; G01N 21/314; G01N 21/85; G01N 21/94; G01N 33/025; G01N 33/10; A01F 12/44; A01F 12/48; A01F 12/50; A01B 79/005
USPC ....... 209/576, 577, 587; 250/339.07, 339.11; 356/244, 326, 328; 460/7, 59, 119; 701/25, 50, 129
See application file for complete search history.

(56) References Cited

U.S. PATENT DOCUMENTS

| | | | |
|---|---|---|---|
| 6,483,583 | B1 | 11/2002 | Wright et al. |
| 7,169,040 | B2* | 1/2007 | Kormann ............. G01N 21/359 |
| | | | 250/339.11 |
| 8,115,923 | B2* | 2/2012 | Priesnitz ................... G01J 3/02 |
| | | | 356/326 |
| 9,000,319 | B2* | 4/2015 | Deefholts ............... B07C 5/342 |
| | | | 209/576 |
| 9,842,252 | B2* | 12/2017 | Edgerton ........... G06K 9/00496 |
| 2003/0063276 | A1 | 4/2003 | Sjodin |

FOREIGN PATENT DOCUMENTS

| | | |
|---|---|---|
| JP | 2006-081488 A | 3/2006 |
| JP | 2006081488 A | 3/2006 |
| JP | 2006246831 A | 9/2006 |
| JP | 3828837 B | 10/2006 |
| JP | 2007-074963 A | 3/2007 |
| JP | 4057196 B | 3/2008 |

* cited by examiner

COMBINE

CROSS-REFERENCE TO RELATED APPLICATIONS

This application is the U.S. national phase of International Application No. PCT/JP2014/052537 filed Feb. 4, 2014, and claims priority to Japanese Patent Application No. 2013-093920 filed Apr. 26, 2013, the disclosures of which are hereby incorporated in their entirety by reference.

TECHNICAL FIELD

The present disclosure relates to a combine that reaps grain culm from a field while traveling, threshes the reaped grain culm and then accumulates resultant grains in a grain tank.

BACKGROUND ART

There has been proposed a combine configured to effect a weight measurement or a moisture measurement on grains stored in a grain tank and then to output the result as harvest information of harvested grains. For instance, in the case of a combine disclosed in Patent Document 1, the combine includes a moisture measurement device configured to take in some of grains supplied to a grain tank and to measure a moisture amount thereof and a load cell configured to detect a load of the grain tank. During a harvesting travel of this combine, calculation of a reaping area from a travel speed, a travel time and a reaping width and calculation of increase (increment) in a grain weight per this reaping area are effected in repetition, whereby a yield distribution per unit segment of a field is outputted. However, if such grain weight increase is measured from the load of the grain tank, as the weight of grains is small as compared with the weight of the grain tank, significant cost will be required for realization of a measurement mechanism capable of accurate measurement of small increment in the grain weight. Without accurate measurement of small increment in the grain weight, it will become difficult to evaluate harvesting failure in a very small segment of the field, due to such factors as irregularities of exposure to sunshine, fertilization, etc.

Patent Document 2 discloses a combine having a yield detection device configured to measure yield of grains per unit time for the purpose of adjustment control of a sorting device. This yield detection device consists of a cylinder body, a shutter for opening and closing a lower opening of the cylinder body and a pressure sensor provided inside the cylinder body and the yield detection device is configured such that a time until accumulation of grains up to the position of the sensor is measured and then based on this measured time, a yield per unit time of the grain is determined. With this combine, the sorting device is controlled merely such that the greater the grain volume per unit time passing this sorting device, the greater the processing amount of the sorting device. As such, no consideration is given to such factor as a travel speed of the combine, which factor causes variation in the yield per unit time, irrespectively of e.g. growth condition of grain culm (ripening state of grains).

BACKGROUND ART DOCUMENTS

Patent Documents

Patent Document 1: Japanese Unexamined Patent Application Publication No. 2006-081488 (FIG. 5, FIG. 14, FIG. 17)

Patent Document 2: Japanese Unexamined Patent Application Publication No. Hei. 3-47014 (page 3, left-lower column, line 6 to page 4, right-upper column, line 20, FIG. 1)

SUMMARY

Problems to be Solved by Invention

In view of the above-described state of the art, in regards to a combine that reaps grain culm from a field while traveling, threshes the reaped grain culm and then accumulates resultant grains in a grain tank, there is a need for a technique that allows accurate harvest evaluation of each of a plurality of segments of a field.

Solution

In a combine that reaps grain culm from a field while traveling, threshes the reaped grain culm and then accumulates resultant grains in a grain tank, according to the present invention, the combine comprises:

a yield measurement container having a yield receiving opening for receiving at least some of grains supplied to the grain tank, a yield discharge opening for discharging received grains, and a yield shutter for opening and closing the yield discharge opening;

a yield measurement section for detecting, while the yield shutter is closed, that a predetermined volume of grains has been accumulated in the yield measurement container and then outputting a detection signal;

a time calculation section for calculating, based on the detection signal, an accumulating time required to accumulate the predetermined volume of grains; and a yield calculation section for calculating a yield per unit travel based on a travel speed and the accumulation time.

With the above-described configuration, the time (accumulation time) until grains supplied to the grain tank reach a predetermined volume (capacity) in the yield measurement container is calculated. Therefore, based on this time and a travel speed of the combine, a travel distance with which the predetermined volume of grains can be accumulated, in other words, a yield per unit travel, which is defined as a "yield per unit travel", is calculated. Namely, a yield for a small segment of the field is obtained. In this, in case the yield receiving opening of the yield measurement container is capable of receiving only some of the grains supplied to the grain tank, as long as the ratio of the receivable amount is known in advance, with adjustment of the calculated accumulation time based on this ratio, the actual yield per unit travel can be obtained. With use of the above calculation method which is based on a ratio between a supply amount to the grain tank and the receivable amount, it becomes possible to reduce the grain accumulation volume of the yield measurement container. As a result, its configuration can be made compact advantageously. Further, if the grain accumulation volume for use in the calculation of the yield per unit travel is small, the weight to be measured will be made correspondingly small also. In comparison with the conventional technique which measures the weight of accumulated grains including the weight of the grain tank, conditions required for accurate measurement will be lenient. Moreover, since the yield is derived from the volume occupied by grains accumulated per unit time, it is possible to avoid error due to e.g. adhesion of raindrops, which may occur at the time of weight measurement.

As information of harvested grains such as rice, wheat, in addition to a yield, a taste value such as moisture, protein, are also important. If this taste value can be measured for each small segment of the filed, it becomes possible to evaluate an influence of sunshine exposure, fertilization condition, etc. to the taste value, so that fine and detailed farm management is made possible. In order to realize this measurement of a taste value for each small field segment with as simple as possible configuration, according to one preferred embodiment of the present invention:

the combine further comprises:

a taste measurement container having a taste discharge opening for discharging the grains received through the yield discharge opening and a taste shutter for opening and closing the taste discharge opening; and a taste measurement section for measuring, while the taste shutter is closed, a taste value of the grains held in the taste measurement container. With this configuration, since the yield measurement container is utilized as a grain receiving portion for the taste measurement container, the configuration of the taste measurement container can be made simple.

In particular, if at least a portion of the predetermined volume of grains which has been used for the calculation of the yield per unit travel is utilized for the taste measurement by the taste measurement section, this can ensure that the grains for use in the measurement of the yield per unit travel and the grains for use in the measurement of the taste value are from a same small field segment. Therefore, by recording the respective measurement data as one data set in correlation with each other, the yield and the taste value for each small field segment can be stored and accumulated in a reliable manner, without separation from each other.

With a combine, there occurs a time difference (time lag) between the reaping time point of grains to be measured and the measurement time point of the yield or taste value. That is, the travel position of the combine at the time of measurement will not be the position at which the measured grains were harvested, but a position offset by the distance traveled during such time difference. In order to avoid this problem, according to one preferred embodiment of the present invention, the data set and a specific position are adjusted to eliminate the above time difference, based on a processing time measured from grain culm detection by a plant foot sensor for detecting grain culm to be firstly reaped to arrival of the resultant grain at the yield measurement container and the travel speed.

For normal taste measurement, it is required to keep grains to be measured under a stationary condition for a predetermined time. For this reason, in case grains accumulated in the yield measurement container for the yield measurement are to be used directly for the taste measurement as the subsequent step, efficiency will be improved by effecting accumulation of grains for measuring the yield per unit travel, in the course of the taste measurement. In this, if the yield measurement container has a capacity capable of accumulating grains which are supplied to the yield receiving opening during the measurement time of the taste measurement container, inconvenience of grains dropping from the yield measurement container after becoming full can be prevented advantageously.

In case both the yield measurement container and the taste measurement container are provided, the yield measurement container and the taste measurement container can be comprised of a cylinder body which is coaxial and unitary. With this, the configuration can be made simple, advantageously.

According to one mode of the present invention, the yield per unit travel to be calculated is a yield per unit area. By calculating the yield per unit area defined by the reaping width and a small travel distance of the combine one after another and then displaying or recording them, it becomes possible to grasp variation in the yield by the travel of the combine, that is, change in the field position and change in the yield. In particular, by recording the travel track of the combine at the time, it becomes possible to evaluate a yield at a desired position in the field.

According to another mode of the present invention, the yield per unit travel to be calculated is a yield per unit segment divided from the field. In this case, in particular, if one side of the unit segment is used as the reaping width of the combine and another side of the unit segment is used as the travel distance with which the yield per unit travel can be obtained, it becomes possible to utilize the calculated yield per unit travel directly as the yield per unit segment, thus being advantageous for data processing.

EMBODIMENTS OF THE INVENTION

Before specific embodiments of a combine according to the present invention are explained, a basic principle that characterizes the present invention will be explained with reference to FIG. 1.

Figure 1:
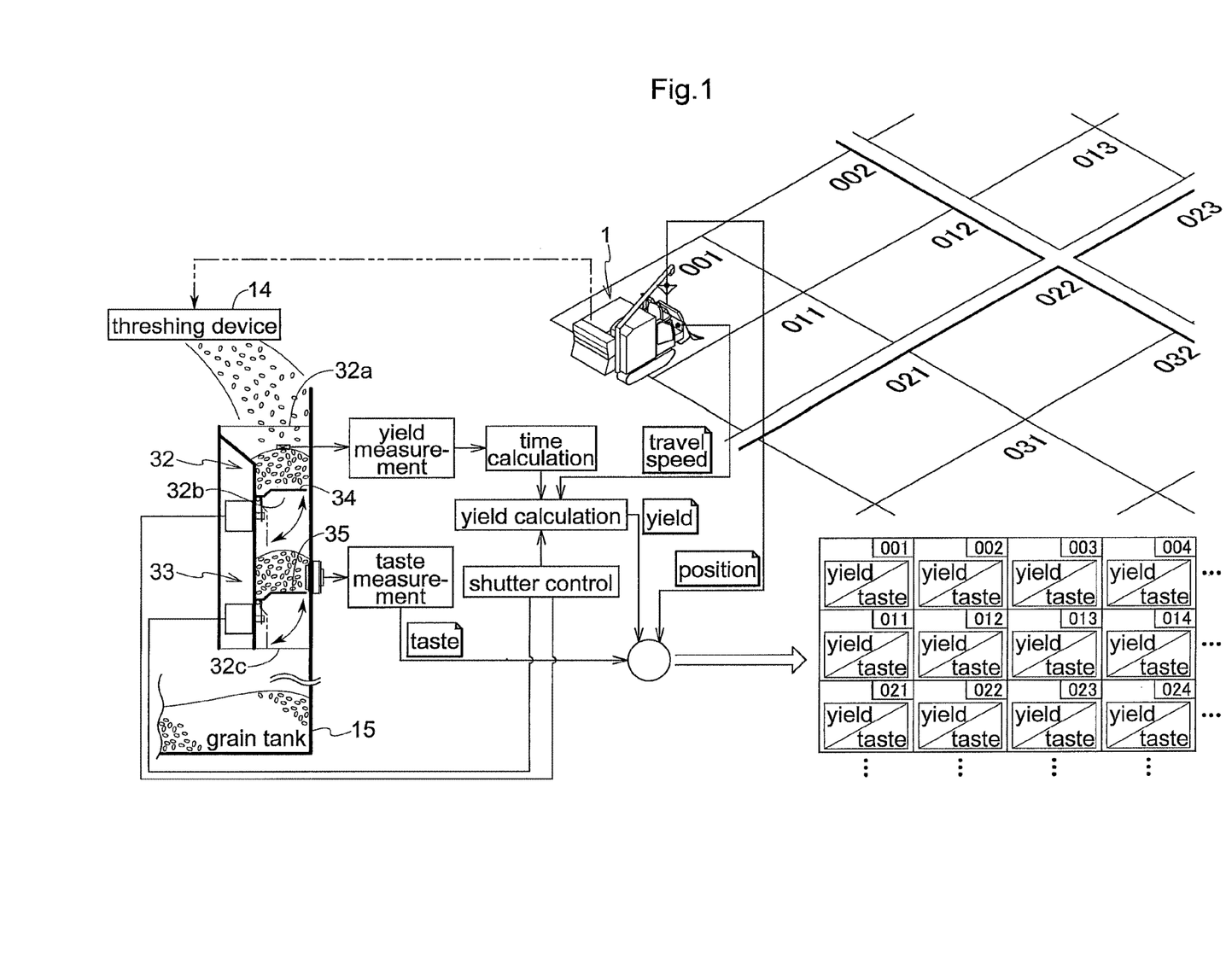
FIG. 1 is a diagram for explaining a basic configuration of the present invention.

In the example illustrated in FIG. 1, a combine 1 reaps and harvests grain culm of wheat or rice while traveling in a field and threshed grains are stored in a grain tank 15 mounted on the combine 1. In this, with this combine 1, an amount (volume) of grains supplied to the grain tank 15 over time, that is, a "yield", is measured. Further, the taste (moisture, protein content, etc. thereof) can also be measured.

For the yield measurement of grains, the grain tank 15 is provided with a yield measurement container 32 which has a yield receiving opening 32a for receiving at least some of grains supplied to this grain tank, a yield discharge opening 32b for discharging the received grains and a yield shutter 34 for opening and closing the yield discharge opening 32b. The yield measurement container 32 is configured such that its yield receiving opening 32a is disposed so as to face a flow of grains which are sent continuously from a threshing device to the grain tank 15 during a reaping operation. The yield shutter 34 is switchable between a closing posture for shutting the yield discharge opening 32b formed at a position (a vertical position in the perpendicular direction in this case) facing the yield receiving opening 32a of the yield measurement container 32 and an opening posture for opening this yield discharge opening 32b. Therefore, when the yield shutter 34 assumes the closing posture, grains will be progressively accumulated over time inside the yield measurement container 32. The yield measurement container 32 includes a yield measurement section for detecting that a predetermined volume of grains has been accumulated in the yield measurement container 32 and then outputs an appropriate volume detection signal indicating accumulation of the predetermined volume of grains. A time period from switchover of the yield shutter 34 to the closing posture until output of the above detection signal is an "accumulation time" required for accumulation of the predetermined volume of grains. If this accumulation time is calculated and a travel speed of the combine 1 during this time is obtained, then, based on this travel speed and the accumulation time, a "yield per unit travel" which is a yield obtained during per unit travel, is calculated. By effecting calculation of this yield per unit travel in repetition during reaping travel of the combine 1, it is possible to assign the yield per unit travel in correlation to each travel position of the combine 1. Then, based on the yield per unit travels assigned to the respective travel positions, yields for respective predetermined travel distances, or, yields for respective predetermined segments obtained by dividing the field to a predetermined size, that is, yield distribution in the field can be obtained.

In the case of the example shown in FIG. 1, a taste measurement container 33 is provided downwardly of the yield measurement container 32 in the flow direction of grains. This taste measurement container 33 includes a receiving opening which is formed by the above-described yield discharge opening 32b and a taste discharge opening 32c which is opened and closed by a taste shutter 35. When the predetermined volume of grains has been accumulated in the yield measurement container 32, if the taste shutter 35 is switched to the closing posture and the yield shutter 34 is switched to the opening posture, the grains accumulated in the yield measurement container 32 will be held temporarily inside the taste measurement container 33. The yield measurement container 32 includes a taste measurement section for measuring a taste value (a moisture content, a protein content, etc.) of these stored grains. With this arrangement, the taste of the grains whose yield has been measured by the yield measurement container 32 is measured also. Incidentally, in the course of the above, if the accumulated grains have turned out excessive, by adjusting the timing of switching the taste shutter 35 to the closing posture, it becomes also possible to use only some of the accumulated grains as subject for the taste measurement. Namely, since at least some of a predetermined volume of grains which has been used for calculation of the yield per unit travel is used for the taste measurement by the taste measurement section and also since it is possible to avoid stay of grains in the yield measurement container 32, it is possible to correlate a yield per unit travel and a taste value corresponding to each other as a data set of grains harvested at a specific position of the field. By obtaining such data set in repetition during reaping travel of the combine 1, there is generated harvest information for evaluation of distributions of yields and taste values in the field and such harvest information will be recorded in the combine 1 or in a remotely located server.

In order to assign a yield and a taste of grains harvested therein to a specific reaping area (field segment), it is necessary to take into consideration a time lag from the reaping of grain culm to measurement on grains resultant therefrom. This time lag can be calculated, based on a processing time measured from the time of detection by a plant foot sensor of grain culm to be firstly reaped and arrival of resultant grain thereof at the yield measurement container 32 and a travel speed of the combine 1. By using the calculated time lag, accurate matching can be made between the data set consisting of a yield and a taste with a specific position.

Figure 2:
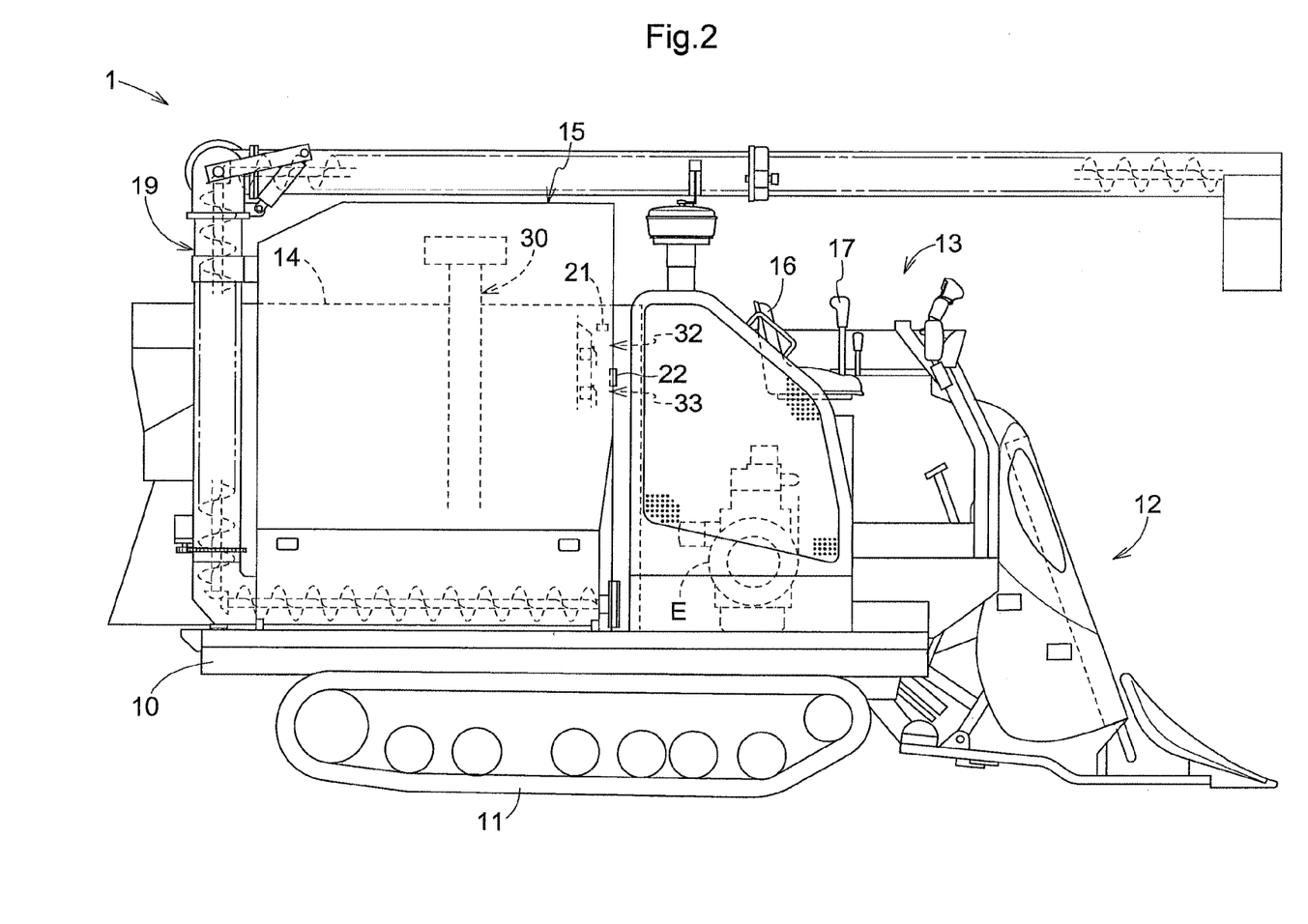
FIG. 2 is a side view showing one embodiment of a combine according to the present invention.
Figure 3:
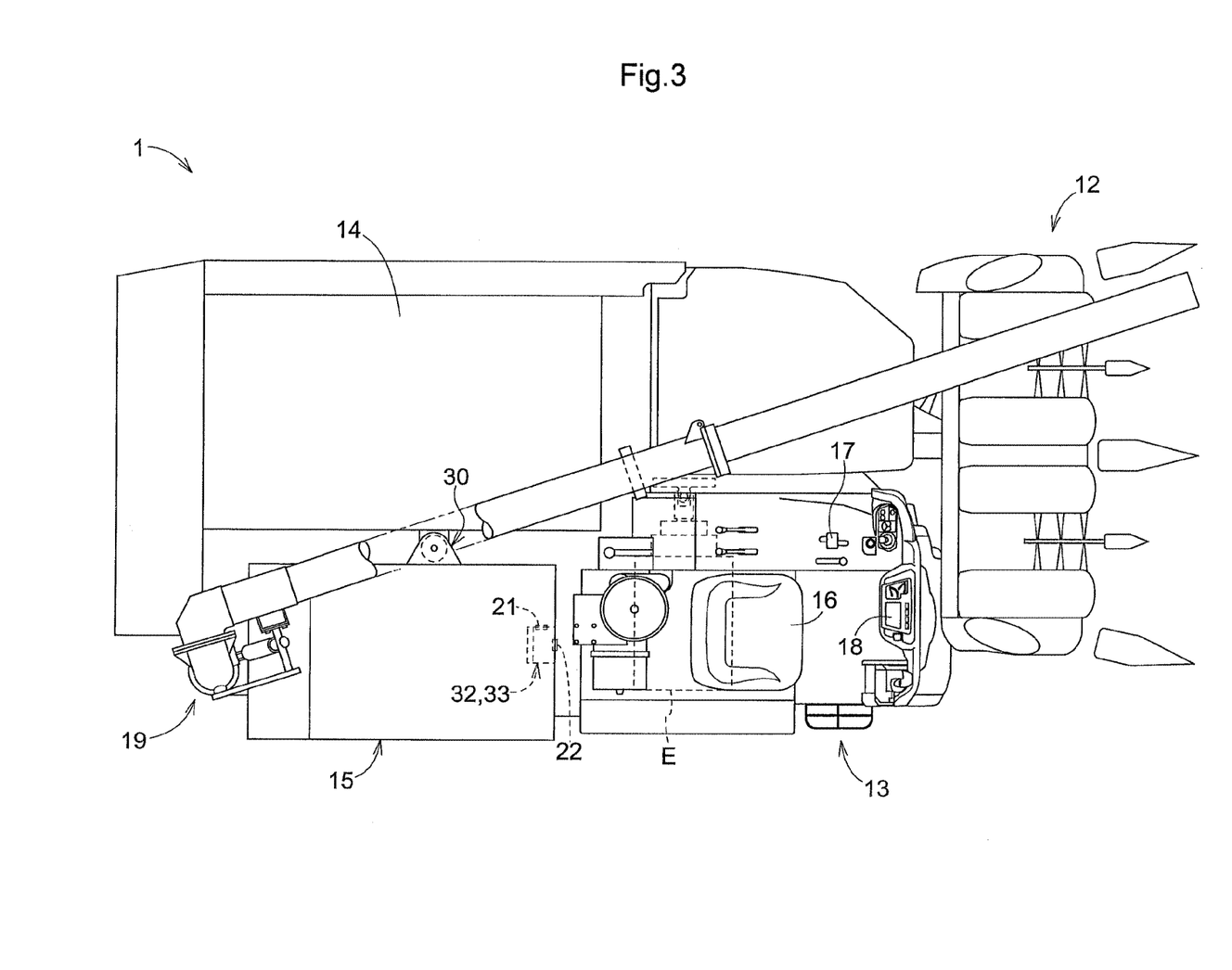
FIG. 3 is a plan view of the combine shown in FIG. 2, FIG. 4A and FIG. 4B are diagrams showing a yield measurement section and a taste measurement section which are mounted on the combine of FIG. 2.

Next, with reference to the accompanying drawings, one specific embodiment of the combine according to the present invention will be explained. FIG. 2 is a side view of the combine 1 and FIG. 3 is a side view of the combine 1.

The combine 1 includes a vehicle body frame 10 comprised of a plurality of steel members such as channel members or angular pipes connected to each other. Downwardly of the vehicle body frame 10, a pair of left and right crawlers 11 are mounted. On a forward side of a right half portion of the vehicle body frame 10, an engine E is mounted and a driver's section 13 is formed upwardly thereof. In the driver's section 13, there are disposed a driver's seat 16, a control lever 17, etc. At a front end on the left side of the vehicle body frame 10, there is provided a reaping section 12 configured to reap grain culm to be harvested present forwardly of the vehicle body at the time of a working travel and then to convey reaped grain culm rearwards. In the left half portion of the vehicle body frame 10, there is mounted a threshing device 14 configured to receive reaped grain culm conveyed by the reaping section 12 and to effect a threshing processing on grain-bearing portions of the reaped grain culm while conveying these rearwards and then to effect a sorting processing on grains obtained by the above threshing processing. On the rear side of the right half portion of the vehicle body frame 10, there is mounted a grain tank 15 formed of plate metal and configured to accumulate therein grains which have been conveyed by lifting via a screw-lift type feeding conveyer 30 from the threshing device 14. The grain tank 15 mounts therein a grain discharge device 19 for discharging grains accumulated in the grain tank 15 to the outside of the vehicle. Though shown only schematically in FIG. 2 and FIG. 3, inside the grain tank 15, there are disposed a yield measurement section 21 for measuring a yield of grains and a taste measurement section 22 for measuring a taste of the grains.

Figure 4A:
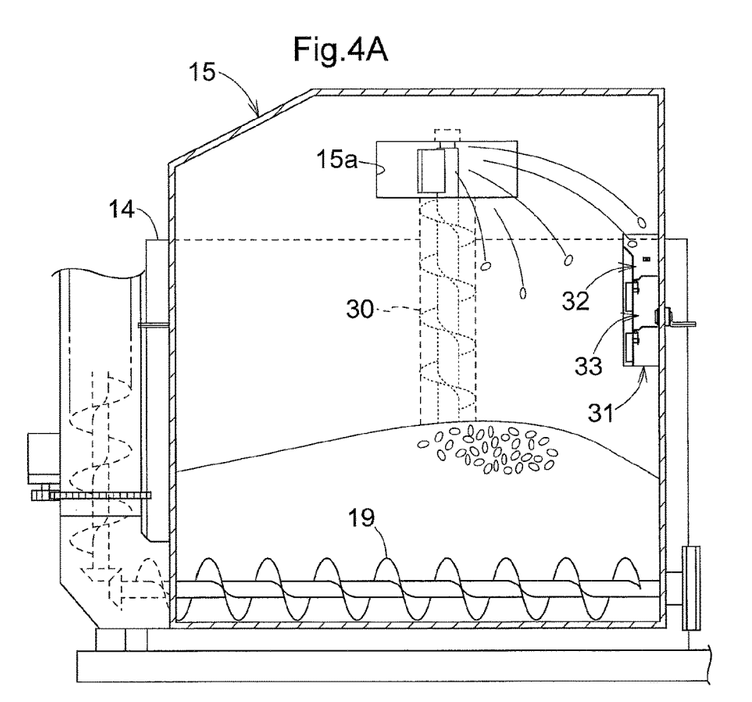
Figure 4B:
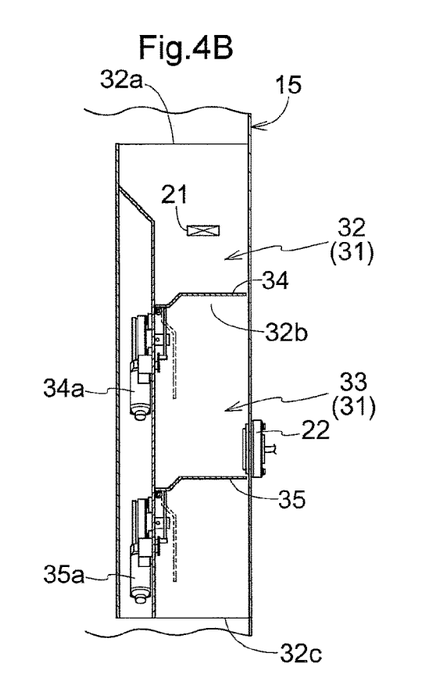

As shown schematically in FIG. 4A and FIG. 4B, yield measurement and taste measurement are effected on grains which are introduced via an inlet 15a into a yield measurement container 32 and a taste measurement container 33 which are attached to the inside of the grain tank 15. In this embodiment, as shown in FIG. 4A and FIG. 4B, an upper half of a cylinder body 31 attached to a lateral wall of the grain tank 15 is used as the yield measurement container 32 and a lower half of this cylinder body 31 is used as the taste measurement container 33. That is, the yield measurement container 32 and the taste measurement container 33 are formed integral as the cylinder body 31, with the taste measurement container 33 being located below the yield measurement container 32. And, an upper opening of the cylinder body 31 acts as a yield receiving opening 32a of the yield measurement container 32. At a yield discharge opening 32b forming the lower end of the yield measurement container 32, a yield shutter 34 is provided. This yield shutter 34 can be pivoted by an actuator 34a between a closing posture for shutting the inside space of the cylinder body 31 along the transverse direction and an opening posture for allowing passage of grains through the inside space. The yield measurement container 32 and the taste measurement container 33 are formed continuously in the vertical direction, so that the yield discharge opening 32b acts also as a taste receiving opening of the taste measurement container 33. Similarly, at a taste discharge opening 33b forming the lower end of the taste measurement container 33, a taste shutter 35 is provided. This taste shutter 35 too can be pivoted by an actuator 35a between a closing posture for shutting the inside space of the cylinder body 31 along the transverse direction and an opening posture for allowing passage of grains through the inside space.

The yield receiving opening 32a of the yield measurement container 32 is disposed at a position which is reached by some of grains which have been conveyed by the feeding conveyer 30 from the threshing device 14 and discharged through the inlet 15a to the grain tank 15 by blades. Therefore, when the yield shutter 34 is pivoted to the closing posture, grains flying from the inlet 15a will enter the yield measurement container 32 through the yield receiving opening 32a and begin to be accumulated on the yield shutter 34 which is currently shutting the yield discharge opening 32b. The yield measurement container 32 includes a proximity sensor as the yield measurement section 21, which outputs an "appropriate volume detection signal" when a predetermined volume of grains has been accumulated in the yield measurement container 32.

Upon pivotal switchover of the yield shutter 34 of the yield measurement container 32 which has accumulated therein the predetermined volume of grains to the opening posture, these grains accumulated in the yield measurement container 32 will now enter the taste measurement container 33. At this time, if the taste shutter 35 currently assumes the closing posture, the grains will be kept inside the taste measurement container 33. As this taste measurement container 33 includes the taste measurement section 22, a taste of the grains held therein is measured. In this embodiment, the taste measurement section 22 employs a spectroscopy technique, so that measurement of a grain moisture value or protein value is possible. From the taste measurement section 22, a taste value can be outputted which includes at least one of a measurement value relating to such grain component as a moisture content or a protein content and a taste calculated value obtained from a ratio of such components.

Figure 5:
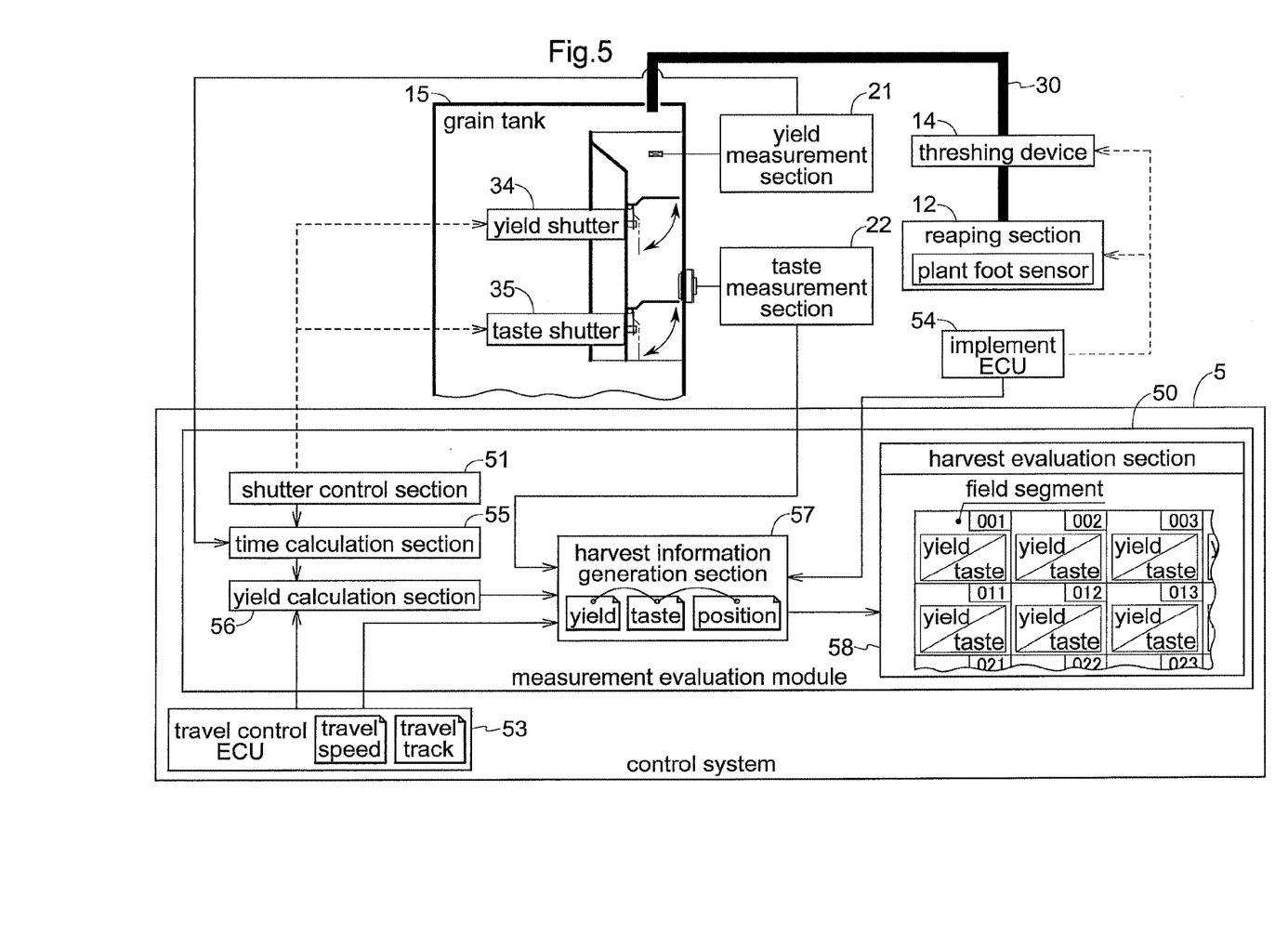
FIG. 5 is a functional block diagram for explaining harvest information generation by a controller mounted on the combine shown in FIG. 2, FIG. 6 are a timing chart of yield measurement and a diagram showing movements of a shutter.

FIG. 5 shows a functional block diagram for explaining a control system relating to yield measurement and taste measurement in this combine 1. This control system is based substantially on the basic principle illustrated in FIG. 1. Functional sections constructed in a control system 5 mounted on the combine 1 and particularly relating to the present invention are a travel control ECU (electronic control unit) 53, an implement ECU 54 and a measurement evaluation module 50. Essentially, these functions are realized by execution of a program, but, when necessary or appropriate, a hardware can also be used therefor. These functional sections are connected with each other via an in-vehicle LAN. Further, the measurement evaluation module 50 is connected to the yield measurement section 21, the taste measurement section 22, the yield shutter 34 and the taste shutter 35 which are provided in the grain tank 15.

The travel control ECU 53 is an ECU which handles various control information relating to vehicle travel and has functions for preparing data, obtained from an unillustrated sensor management module, via an in-vehicle LAN, such as a travel speed, a travel distance, a travel track, an engine speed, a fuel consumption, etc. into "travel information". The implement ECU 54 is an ECU for controlling reaping or harvesting devices such as the reaping section 12 and the threshing device 14. The implement ECU 54 has functions for preparing data indicating the operation status or the working status of various devices into "travel information".

Incidentally, the signal from the plant foot sensor 12a which detects execution of an actual reaping operation is transmitted to the measurement evaluation module 50 via the implement ECU 54. Further, though not shown, this control system 5 includes a display ECU for controlling information display on a monitor or a metering panel and a communication ECU for effecting data exchange with an external device (including a remotely located server).

The measurement evaluation module 50 includes a shutter control section 51, a time calculation section 55, a yield calculation section 56, a harvest information generation section 57 and a harvest evaluation section 58. The shutter control section 51 controls the yield shutter 34 and the taste shutter 35 to either the closing posture or the opening posture thereof. The time calculation section 55 calculates an "accumulation time" which is defined as a time period measured from switchover of the yield shutter 34 to the closing posture to accumulation of the predetermined volume of grains in the yield measurement container 32 (to input of the appropriate volume detection signal from the yield measurement section 21). The yield calculation section 56 can calculate a yield per unit travel time from the accumulation time and the predetermined value or a yield per unit travel distance from the accumulation time and a travel speed. The yield per unit travel distance can also be calculated directly a direct travel distance measured within the accumulation time and the predetermined volume in case the travel distance of the combine 1 is measured. These yields per unit time and per unit distance are one embodiment of "a yield per unit travel" which is defined as a yield obtained during per unit travel in the context of the present invention.

The harvest information generation section 57 generates harvest information of each measurement by linking or correlating taste data obtained from the taste measurement section 22, yield data (yield per unit travel) obtained from the yield calculation section 56 with travel data obtained from the travel control ECU 53 such as a travel distance, a travel position, etc. In this, there occurs a time lag (time difference) between the timing of measurement of grains as the measurement target and the timing of harvesting of these grains.

Therefore, there is a need to adjust this. This time difference can be obtained by calculating a time from detection of grain culm by the plant foot sensor 12 at the time of start of harvesting operation and arrival of the grain threshed from the grain culm at the grain tank 15. The harvest evaluation section 58 assigns the harvest information generated by the harvest information generation section 57 to each field segment obtained by dividing the field, thus generating field distribution information of yields and tastes. Incidentally, it is also possible to employ a mode in which the above yield evaluation section 58 is constructed in an external computer and harvest information is transmitted from the harvest information generation section 57 to this harvest evaluation section 58 via a communication network. Further alternatively, the harvest information generation section 57 and the harvest evaluation section 58 can be combined into a single unit which provides either one or both of the above functions.

Next, with reference to the timing chart and state transitions of the yield measurement container 32 and the taste measurement container 33 illustrated in FIG. 6, there will be explained one example of flow of control in the yield measurement and the taste measurement.

At an initial condition when a reaping operation is not yet started, the yield shutter 34 and the taste shutter 35 are set to the opening posture respectively. When a timing for discharging grains into the grain tank 15 comes after start of a reaping operation, the yield shutter 34 is switched to the closing posture, upon which accumulation of grains in the yield measurement container 32 is initiated. Simultaneously, time measurement (generation of count signals) by the time calculation section 55 is started. When the volume of grains accumulated in the yield measurement container 32 reaches the predetermined volume, the proximity sensor 21 as the yield measurement section 21, is activated to output an appropriate volume detection signal.

As being triggered by the generation of this appropriate volume detection signal, the time measurement by the time calculation section 55 is stopped and also the yield shutter 34 is switched to the opening posture and the taste shutter 35 is switched to the closing posture. The time measurement value obtained by the time calculation section 55 is the time period until the predetermined volume of grains is accumulated in the yield measurement container 32 (this time period is denoted by a mark: t1 in FIG. 6). Here, if the predetermined volume is (q), then, there is obtained a yield per unit time of: q/t1.

By the switchover of the yield shutter 34 to the opening posture and the switchover of the taste shutter 35 to the closing posture, the grains which have been accumulated in the yield measurement container 32 are now moved into the taste measurement container 33. Incidentally, the taste shutter 35 can be switched over to the closing posture in advance.

At the timing of completion of movement of all the grains of the yield measurement container 32 into the taste measurement container 33 subsequent to the switchover of the yield shutter 34 to the opening posture, the yield shutter 34 is switched back to the closing posture, upon which grains will be started to be accumulated in the yield measurement container 32. Simultaneously, time measurement by the time calculation section 55 (generation of count signals) is started. In the taste measurement container 33, taste measurement is started. In this, measurement of a moisture content value or a protein content value is effected through wavelength analysis of light beam irradiated onto grains. Measurement time required for the taste measurement is about few seconds to a few tens of seconds.

Upon completion of the taste measurement, the taste shutter 35 is switched to the opening posture, whereby grains inside the taste measurement container 33 are discharged into the grain tank 15. The above-described predetermined volume in the yield measurement container 32 is set as a volume greater than the volume of grains that can be received into yield measurement container 32 during this taste measurement. Again, when the volume of grains accumulated in the yield measurement container 32 reaches the predetermined volume, the appropriate volume detection signal is generated and also, as described above, the time measurement by the time calculation section 55 is stopped and the yield shutter 34 is switched to the opening posture and the taste shutter 35 is switched to the closing posture. The accumulation time of the second yield measurement is denoted by a mark: t2 in FIG. 2. In this way, during a reaping operation, yields per unit time and taste values are obtained one after another.

Figure 7:
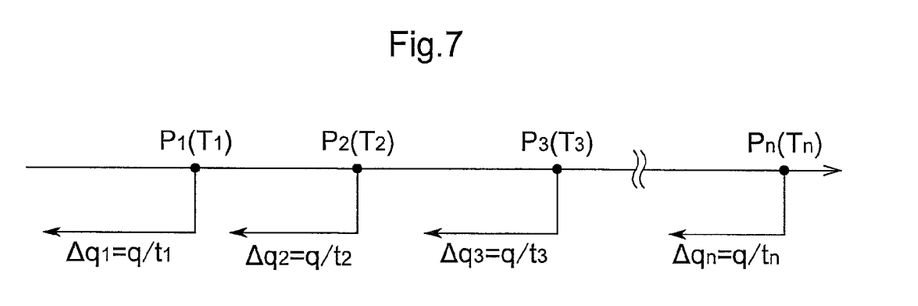
FIG. 7 is an explanatory view of calculation of yield per unit time.

Depending on a position in the field, that is, on a segment divided finely from the field, the growth condition of crops such as rice or wheat will differ. Therefore, the yields per unit time obtained one after another in the above-described manner will vary in accordance with position in the field. This is schematically illustrated in FIG. 7. Here, marks: T1, T2 . . . denote times measured from timing of completion of yield measurement (time measurement) of each cycle backwards to the timing (timing of harvest of grains from the field) of conveyance of grains from the reaping section 12 to the yield measurement section 21 (that is, the time lag described above). Marks: P1, P2 . . . denote travel distances from each position or start of operation by the combine 1 in the field at the above timings. The yield per unit time: $\Delta q$ obtained by each cycle of yield measurement is a value obtained by dividing the predetermined volume: q by the measured time value: t obtained by the time calculation section 55. As may be apparent from FIG. 7, in this case, the yield per unit time: $\Delta qn$ ($\Delta q1$, $\Delta q2$ . . . ) obtained at the timing of completion of measurement: Pn (Tn) for a certain cycle:

n is considered effective for the field small segment from the timing of measurement: Pn−1 (Tn−1) for the previous cycle: n−1 to the current. Therefore, from the yields per units: $\Delta q1$, $\Delta q2$ . . . obtained one after another, a yield for any desired field segment can be calculated.

Instead of the above, a different method can be adopted in which a yield per unit time: $\Delta qn$ obtained at a certain timing: Pn (Tn) is caused to correspond to a ½ segment before and after Pn (Tn). Or, a further different method can be adopted in which a yield per unit time: $\Delta qn$ obtained at a certain timing: Pn (Tn) is caused to correspond to an area until the timing: Pn+1 (Tn+1) when the next measurement result can be obtained.

Figure 8:
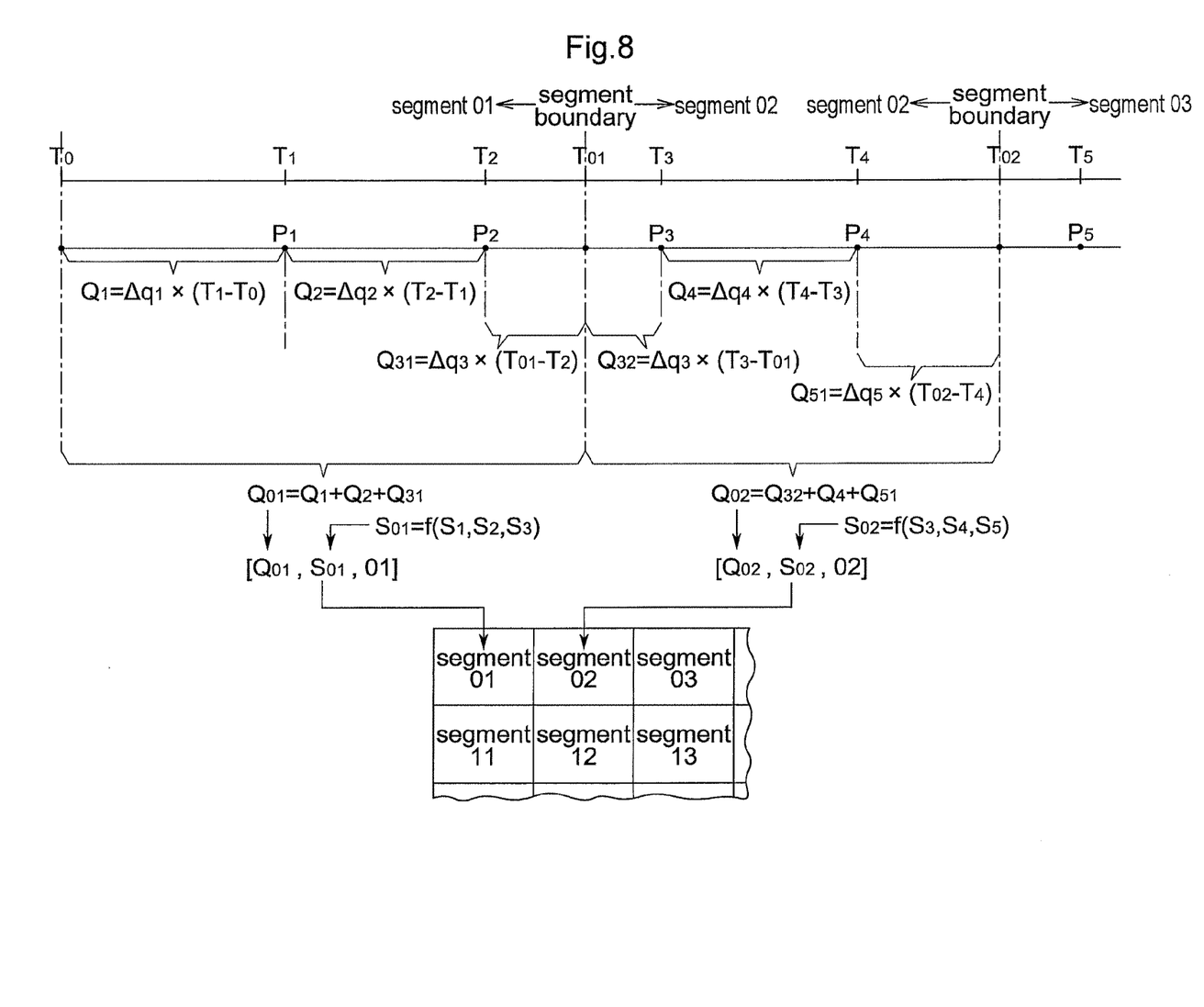
FIG. 8 is an explanatory view of calculation of yield per unit field segment.

FIG. 8 schematically shows how distribution data of yield and taste is produced by assigning yields per unit time: $\Delta q1$, $\Delta q2$ . . . thus obtained and taste measurement values obtained simultaneously to respective field segments.

The segment 01 includes a position P1 and a position P2 corresponding respectively to a timing T1 and a timing T2. And, transition from this segment 01 to a segment 02 occurs at a timing T01. As described above, in the segment 01, to the section to the position P1, $\Delta q1$ is assigned as the yield per unit time, to the section from the position P1 to the position P2, $\Delta q2$ is assigned as the yield per unit time, and further, to the section from the position P2 to the rest, $\Delta q3$ is assigned as the yield per unit time. Therefore, the yield: Q01 for the segment 01 is calculated as follows.

$$Q01 = Q1 + Q2 + Q31,$$

where:

$$Q1 = \Delta q1 \times (T1 - T0),$$

$$Q2 = \Delta q2 \times (T2 - T1),$$

$$Q31 = \Delta q3 \times (T01 - T2).$$

Incidentally, in this embodiment, the accumulated grains which have been used for the calculations of the yields Q1, Q2, Q3 are subjected also to taste measurements, from which taste values S1, S2 and S3 are obtained. Thus, by obtaining an average thereof, a taste value S01 for the segment 01 can be obtained. In this, the ratio of S3 in the segment 01 is smaller as compared with the other two. So, a weighted average taking the weight for the portion can be used.

A data set: [Q01, S01, 01] which correlates the obtained yield: Q01 and a taste value: S01 and an ID (designated here as 01) indicating the segment 01 is assigned as "harvest information" to the field segment map. Harvest information assigned to the respective segments in the manner described above can be visualized in the form of e.g. a distribution graph of yield and taste value.

Incidentally, herein, for the purpose of making explanation simple, the reaping width of the combine 1 is caused to correspond to one side of the unit segment and also the unit travel distance is caused to correspond to another side of the unit segment, so the yield per unit travel is treated directly as the yield per unit segment. However, in case one side of the unit segment is greater than the reaping width of the combine 1 and the combine 1 effects a plurality of times of working travel in a single unit segment, the yield for each segment will be obtained by integrating yields of the plurality of times of travel, based on the traveling tracks of the combine 1.

Other Embodiments (1) In the foregoing embodiment, the yield measurement container 32 and the taste measurement container 33 are formed at different positions in the same cylinder body 31, thus being formed as a single unit. Instead, the yield measurement container 32 and the taste measurement container 33 can be formed as separate structures independent of each other. According to one simple example of such case, a cylinder body 31 for the yield measurement container 32 and a cylinder body 31 for the taste measurement container 33 are provided, thus forming the yield measurement container 32 and the taste measurement container 33 independent of each other. In this case, if the yield measurement container 32 including the yield shutter 34 and the taste measurement container 33 including the taste shutter 35 are configured to be separately attachable and detachable, in comparison with the unitary configuration of the yield measurement container 32 and the taste measurement container 33, detachment and attachment operations at failure can be made simple and maintenance inspection costs can be reduced.

Further, in case only yield measurement is needed, only the yield measurement container 32, the yield shutter 34 and the yield measurement section 21 can be provided whereas the taste measurement container 33, the taste shutter 35 and the taste measurement section 22 can be omitted.

(2) In the foregoing embodiment, as shown in FIG. 4A and FIG. 4B, grains received in the yield measurement container 32 are some of the grains which are conveyed by the feeding conveyor 30. Therefore, it is necessary to obtain in advance the ratio between the grains which are received in the yield measurement container 32 and the grains which are not and to calculate the actual yield from the measured yield based on such ratio. In order to avoid this, it is also possible to employ a configuration in which all of grains conveyed by the feeding conveyor 30 can be received once in the yield measurement container 32.

Figure 6:
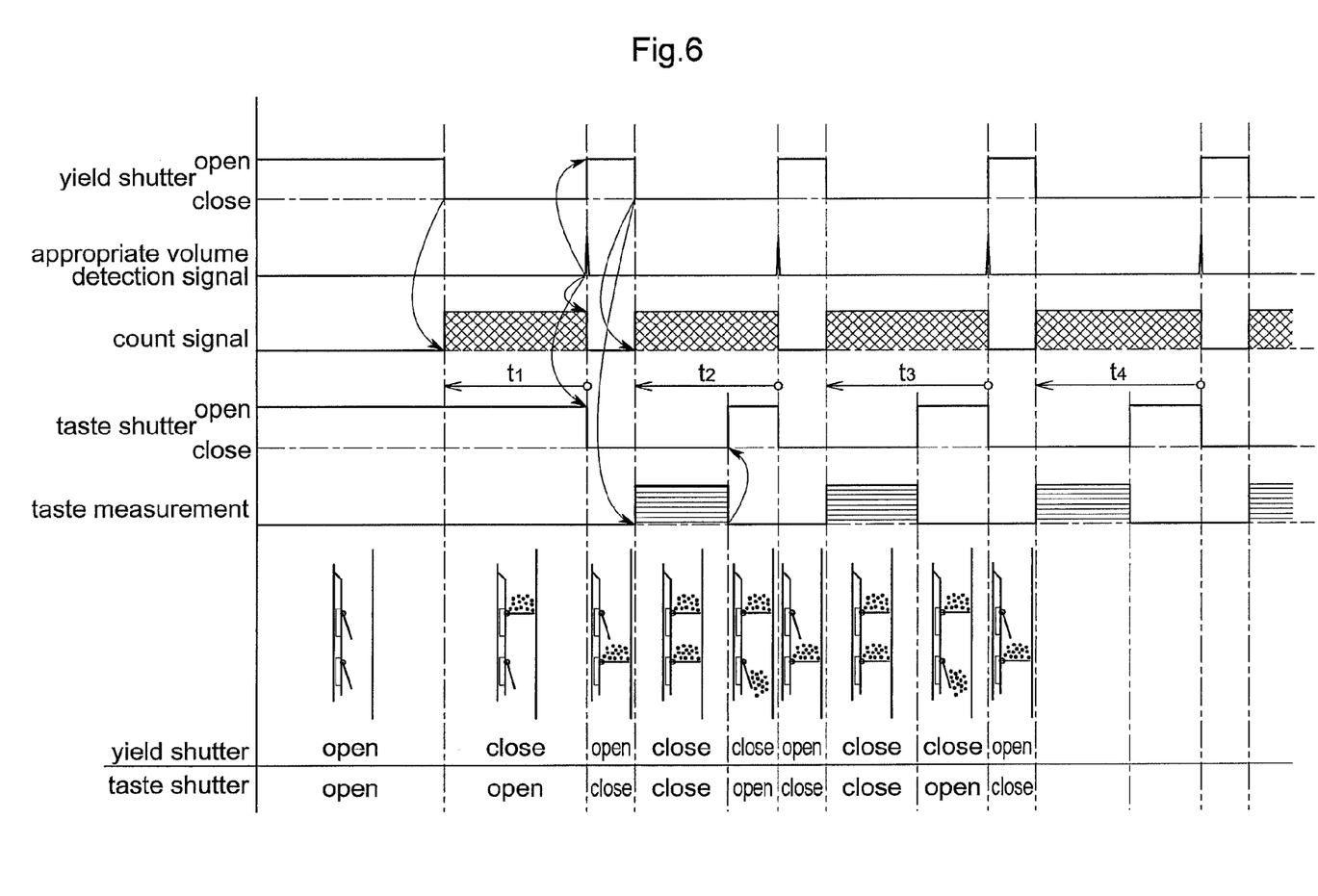

(3) In the foregoing embodiment, as shown in the timing chart of FIG. 6, the yield measurement and the taste measurement are effected substantially continuously. Instead, it is also possible to increase the interval between the respective measurements or to make it possible to change the interval between the respective measurements according to a work condition.

(4) In the foregoing embodiment, the measurement evaluation module 50 is incorporated within the control system 5 of the combine 1. Instead of this, the measurement evaluation module 50 can be constructed as a program of a mobile communication equipment such as a tablet computer or a smart phone to be brought into the combine 1. In such case, data needed to be obtained from the control system 5 and the yield measurement section 21 or the taste measurement section 22 can be transmitted in a wire-less manner via an LAN adaptor included in an in-vehicle LAN of the combine 1. A smart phone, in particular, will be owned and carried by most of drivers and the smart phone is provided with a data transmission function with a communication network with remote places as a standard function thereof. Therefore, generated harvest information can be forwarded to a computer system of a management center and recorded therein easily, thus being advantageous.

(5) In the foregoing embodiment, a proximity sensor is used as the yield measurement section 21. Instead, other sensor or switch can be used which is capable of detecting the predetermined volume of grains being accumulated in the yield measurement container 32. Incidentally, with using such sensor or switch employed as the yield measurement section 21, empty detection of grains in the yield measurement container 32 can be effected, so as to check discharge of accumulated grains by opening of the yield shutter 34. For a similar purpose, such sensor or switch can be provided also in the taste measurement container 33 for effect empty detection of grains, or an appropriate volume detection when appropriate in the taste measurement container 33.

(6) In the foregoing embodiment, an optical type unit is employed as the taste measurement section 22. Instead, any other type such as pulverization type, can be employed also.

Figure 9:
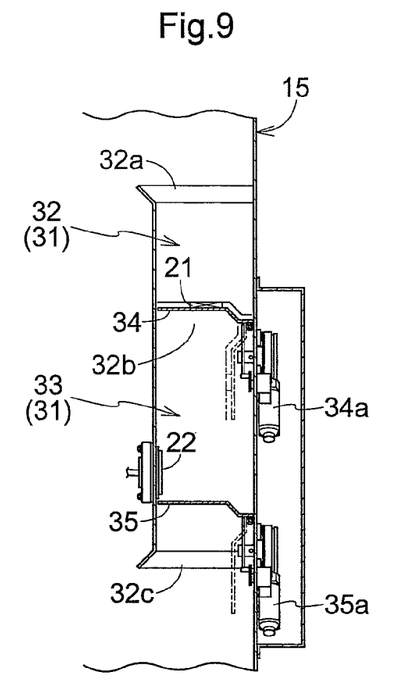
FIG. 9 is a diagram showing a yield measurement section and a taste measurement section according to a further embodiment.

(7) In the foregoing embodiment, as shown in FIG. 4B, the yield measurement container 32 and the taste measurement container 33 are formed along the lateral wall of the grain tank 15 and further the actuators 34a and 35a respectively for the yield shutter 34 and the taste shutter 35 are provided to the lateral face of the tank inner side of the yield measurement container 32 and the taste measurement container 33. Further, the taste measurement section 22 is attached to the inner and outer sides of the lateral wall by providing thorough portion in the lateral wall of the grain tank 15. Instead of this configuration, as shown in FIG. 9, the respective actuators 34a and 35a of the yield shutter 34 and the taste shutter 35 can be provided in the lateral wall of the grain tank 15. In such case, in the case of the example shown in FIG. 9, a through portion is formed in the lateral wall of the grain tank 15, so that the actuators 34a and 35a are provided to the inner side and the outer side of the lateral wall. And, the taste measurement section 22 is provided on the lateral face of the taste measurement container 33 opposite the lateral wall of the grain tank 15. Further, in the further embodiment shown in FIG. 9, instead of the proximity switch and the like, the yield measurement section 21 can be configured to measure a weight of grains accumulated on the yield shutter 21 by means of a load cell disposed between two bottom plates of a yield shutter 21 which is configured as a double-bottom plate structure. In such case, when a yield (capacity) is to be calculated by conversion of a weight, the yield can be obtained more accurately if a moisture correction is effected based on a moisture content value of the grains.

INDUSTRIAL APPLICABILITY

The present invention is applicable to a various types of combine having a grain tank for accumulating therein grains obtained by threshing grain culm reaped from a field while traveling of the combine.

Description of Reference Marks/Numerals

| | |
|---|---|
| 1: | combine |
| 12: | reaping section |
| 14: | threshing device |

Description of Reference Marks/Numerals

| | |
|---|---|
| 15: | grain tank |
| 21: | yield measurement section (proximity switch) |
| 22: | taste measurement section |
| 30: | feeding conveyer |
| 31: | cylinder body |
| 32: | yield measurement container |
| 32a: | yield receiving opening |
| 32b: | yield discharge opening (taste receiving opening) |
| 33: | taste measurement container |
| 33b: | taste discharge opening |
| 34: | yield shutter |
| 35: | taste shutter |
| 31: | shutter control section |
| 53: | travel control ECU |
| 54: | implement ECU |
| 55: | time calculation section |
| 56: | yield calculation section |
| 57: | harvest information generation section |
| 58: | harvest evaluation section |

The invention claimed is:

1. A combine that reaps grain culm from a field while traveling, threshes the reaped grain culm and then accumulates resultant grains in a grain tank, the combine comprising:
 a yield measurement container having a yield receiving opening for receiving some of grains supplied to the grain tank, a yield discharge opening for discharging received grains, and a yield shutter for opening and closing the yield discharge opening;
 a yield measurement section for detecting, while the yield shutter is closed, that a predetermined volume of grains has been accumulated in the yield measurement container and then outputting a detection signal;
 a time calculation section for calculating, based on the detection signal, an accumulating time required to accumulate the predetermined volume of grains; and
 a yield calculation section for calculating a yield per unit travel based on a travel speed and the accumulation time.

2. The combine according to claim 1, wherein as the yield per unit travel, a yield per unit area is calculated.

3. The combine according to claim 1, wherein as the yield per unit travel, a yield per unit segment divided from the field is calculated.

4. A combine that reaps grain culm from a field while traveling, threshes the reaped grain culm and then accumulates resultant grains in a grain tank, the combine comprising:
 a yield measurement container having a yield receiving opening for receiving at least some of grains supplied to the grain tank, a yield discharge opening for discharging received grains, and a yield shutter for opening and closing the yield discharge opening;
 a yield measurement section for detecting, while the yield shutter is closed, that a predetermined volume of grains has been accumulated in the yield measurement container and then outputting a detection signal;
 a time calculation section for calculating, based on the detection signal, an accumulating time required to accumulate the predetermined volume of grains;
 a yield calculation section for calculating a yield per unit travel based on a travel speed and the accumulation time;
 a taste measurement container having a taste discharge opening for discharging the grains received through the yield discharge opening and a taste shutter for opening and closing the taste discharge opening; and
 a taste measurement section for measuring, while the taste shutter is closed, a taste value of the grains held in the taste measurement container.

5. The combine according to claim 4, wherein the yield measurement container has a capacity capable of accumulating grains which are supplied to the yield receiving opening during the measurement time of the taste measurement container.

6. The combine according to claim 4, wherein the yield measurement container and the taste measurement container are comprised of a cylinder body which is coaxial and unitary.

7. The combine according to claim 4, wherein the yield measurement container and the taste measurement container are separate structures which can be detachable independently of each other.

8. The combine according to claim 4, wherein:
 at least a portion of the predetermined volume of grains which has been used for the calculation of the yield per unit travel is utilized for the taste measurement by the taste measurement section; and
 the yield per unit travel and the taste value corresponding to each other are recorded in correlation with each other as a data set of grains harvested at a specific position in the field.

9. The combine according to claim 8, wherein the data set and the specific position are adjusted, based on a processing time measured from grain culm detection by a plant foot sensor for detecting grain culm to be firstly reaped to arrival of the resultant grain at the yield measurement container and the travel speed.

10. The combine according to claim 4, wherein as the yield per unit travel, a yield per unit area is calculated.

11. The combine according to claim 4, wherein as the yield per unit travel, a yield per unit segment divided from the field is calculated.

* * * * *